United States Patent
Brehm et al.

(10) Patent No.: US 9,047,701 B2
(45) Date of Patent: Jun. 2, 2015

(54) 4D CONE BEAM CT USING DEFORMABLE REGISTRATION

(75) Inventors: Marcus Brehm, Erlangen (DE); Timo Berkus, Ennetbaden (CH); Markus Oelhafen, Rohr (CH); Patrik Kunz, Baden (CH); Marc Kachelriess, Nuremberg (DE); Corey E. Zankowski, San Jose, CA (US)

(73) Assignees: VARIAN MEDICAL SYSTEMS, INC., Palo Alto, CA (US); VARIAN MEDICAL SYSTEMS INTERNATIONAL AG, Zug (CH); FRIEDRICH-ALEXANDER-UNIVERSITAET ERLANGEN-NUERNBERG, Erlangen (DE)

(*) Notice: Subject to any disclaimer, the term of this patent is extended or adjusted under 35 U.S.C. 154(b) by 392 days.

(21) Appl. No.: 13/436,908

(22) Filed: Mar. 31, 2012

(65) Prior Publication Data
US 2013/0259338 A1    Oct. 3, 2013

(51) Int. Cl.
*G06K 9/00* (2006.01)
*G06T 11/00* (2006.01)

(52) U.S. Cl.
CPC ......... *G06T 11/008* (2013.01); *G06T 2211/412* (2013.01)

(58) Field of Classification Search
None
See application file for complete search history.

(56) References Cited

U.S. PATENT DOCUMENTS

| | | | |
|---|---|---|---|
| 6,865,248 B1* | 3/2005 | Rasche et al. | 378/8 |
| 2007/0025509 A1* | 2/2007 | Pang et al. | 378/65 |
| 2007/0189591 A1 | 8/2007 | Lu et al. | |
| 2010/0201786 A1* | 8/2010 | Schaefer et al. | 348/47 |
| 2011/0176723 A1 | 7/2011 | Ali et al. | |
| 2011/0206178 A1 | 8/2011 | Van Herk et al. | |
| 2011/0299751 A1 | 12/2011 | Nord et al. | |
| 2011/0311118 A1 | 12/2011 | Shekhar et al. | |
| 2012/0245453 A1* | 9/2012 | Tryggestad et al. | 600/413 |
| 2012/0281897 A1* | 11/2012 | Razifar et al. | 382/131 |

FOREIGN PATENT DOCUMENTS

| | | |
|---|---|---|
| WO | 2006/003002 A2 | 1/2006 |
| WO | 2006/119623 A1 | 11/2006 |

OTHER PUBLICATIONS

T. Li et al., "Four-dimensional cone-beam computed tomography using an on-board imager" Med. Phys., vol. 33, No. 10, 9 pages, Oct. 2006.

S. Leng et al., "Streaking artifacts reduction in four-dimensional cone-beam computed tomography" Med. Phys., vol. 35, No. 10, 11 pages, Oct. 2008.

(Continued)

*Primary Examiner* — Jon Chang
(74) *Attorney, Agent, or Firm* — Vista IP Law Group, LLP

(57) ABSTRACT

A method of obtaining a volumetric image includes obtaining a plurality of volumetric images, the volumetric images generated using respective sets of projection images, wherein the volumetric images and the respective sets of projection images correspond with different respective bins for a physiological cycle, and determining an additional volumetric image using one or more of the projection images from each of the sets that correspond with the different respective bins for the physiological cycle, wherein the act of determining the additional volumetric image is performed using a processor.

45 Claims, 8 Drawing Sheets

(56) References Cited

OTHER PUBLICATIONS

J.-P. Thirion, "Image matching as a diffusion process: An analogy with Maxwell's demons", Medical Image Analysis, vol. 2, No. 3, 18 pages, Sep. 1998.
H. Wang et al., "Validation of an accelerated 'demons' algorithm for deformable image registration in radiation therapy", Phys. Med. Biol., vol. 50, No. 12, 20 pages, Jun. 2005.
J. Lu et al., "Four-dimensional cone beam CT with adaptive gantry rotation and adaptive data sampling", Med. Phys., vol. 34, No. 9, 10 pages, Sep. 2007.
T. Li et al., "Motion correction for improved target localization with on-board cone-beam computed tomography" Phys. Med. Biol., vol. 51, No. 2, 2 pages, Feb. 2006.
S. Rit et al., "On-the-fly motion-compensated cone-beam CT using an a priori model of the respiratory motion" Med. Phys. vol. 36, No. 6, 8 pages, Jun. 2009.
T. Li et al., "Enhanced 4D cone-beam CT with inter-phase motion model" Med. Phys., vol. 51, No. 9, 8 pages, Sep. 2007.
International Search Report and Written Opinion dated Jul. 8, 2013 for PCT Application No. PCT/US2013/034706, 9 pages.

* cited by examiner

4D CONE BEAM CT USING DEFORMABLE REGISTRATION

FIELD

This application relates to systems and methods for obtaining one or more volumetric images.

BACKGROUND

Sometimes, for diagnostic purpose and/or for radiation treatment planning, the target region of the patient may be imaged using a CT system. For the case in which the target region moves in a periodic motion (e.g., due to breathing), the CT system may be used to determine volumetric images of the target when the target is at different breathing states, so that the volumetric images may be played back as a video stream. One such imaging technique is known as 4D cone beam CT (CBCT). For such purpose, projection images of the target, when the target is at different breathing states, are acquired. A breathing monitoring device is used to determine breathing states of the patient as the CT system acquires the projection images.

After the imaging session, the projection images are then sorted into different sets according to the recorded breathing states of the patient when the corresponding projection images are acquired. For example, the projection images may be sorted according to the phase of the physiological cycle at which they are generated, so that projection images are sorted into different phase bins. After the projection images are sorted, the projection images in each of the phase bin are then used to reconstruct a volumetric image for that phase bins.

SUMMARY

In accordance with some embodiments, a method of obtaining a volumetric image includes obtaining a plurality of volumetric images, the volumetric images generated using respective sets of projection images, wherein the volumetric images and the respective sets of projection images correspond with different respective bins for a physiological cycle, and determining an additional volumetric image using one or more of the projection images from each of the sets that correspond with the different respective bins for the physiological cycle, wherein the act of determining the additional volumetric image is performed using a processor.

In accordance with other embodiments, a computer product includes a non-transitory medium storing a set of instructions, an execution of which causes a process to be performed, the process comprising obtaining a plurality of volumetric images, the volumetric images generated using respective sets of projection images, wherein the volumetric images and the respective sets of projection images correspond with different respective bins for a physiological cycle, and determining an additional volumetric image using one or more of the projection images from each of the sets that correspond with the different respective bins for the physiological cycle.

In accordance with other embodiments, an apparatus for obtaining a volumetric image includes a processor, wherein the processor is configured for obtaining a plurality of volumetric images, the volumetric images generated using respective sets of projection images, wherein the volumetric images and the respective sets of projection images correspond with different respective bins for a physiological cycle, and determining an additional volumetric image using one or more of the projection images from each of the sets that correspond with the different respective bins for the physiological cycle.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Figure 1:
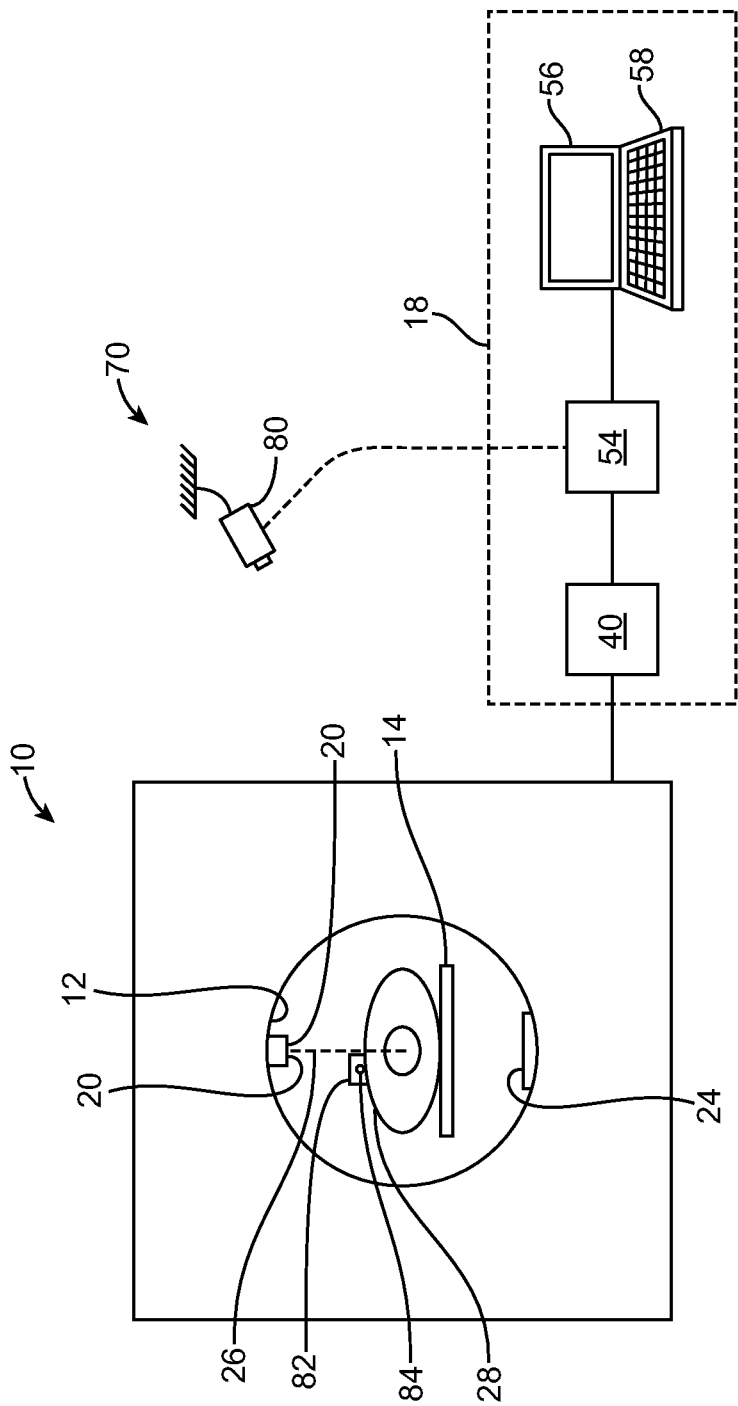
FIG. 1 illustrates a radiation system in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates an imaging system 10 in accordance with some embodiments. The system 10 includes a gantry 12, and a panel 14 for supporting a patient 28. The gantry 12 includes a radiation source 20 that projects a beam 26 of radiation (e.g., x-rays) towards a detector 24 on an opposite side of the gantry 12 while the patient 28 is positioned at least partially between the radiation source 20 and the detector (imager) 24. By means of non-limiting examples, the beam of x-rays can be a cone beam or a fan beam. The detector 24 has a plurality of sensor elements configured for sensing a x-ray that passes through the patient 28. Each sensor element generates an electrical signal representative of an intensity of the x-ray beam as it passes through the patient 28. The system 10 also includes a positioner (not shown) configured to move the radiation source 20. In some embodiments, the positioner may be configured to rotate the gantry 12 to thereby turn the radiation source 20 along a circular or an arc path.

The system 10 also includes a control system 18. In the illustrated embodiments, the control system 18 includes a processor 54, such as a computer processor, coupled to a control 40. The control system 18 may also include a monitor 56 for displaying data and an input device 58, such as a keyboard or a mouse, for inputting data. The operation of the radiation source 20 and the gantry 12 are controlled by the control 40, which provides power and timing signals to the radiation source 20, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

In the illustrated embodiments, the radiation source 20 is a diagnostic radiation source for providing diagnostic energy. In other embodiments, in addition to, or instead of, being a diagnostic radiation source, the radiation source 20 may be a treatment radiation source for providing treatment energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. In further embodiments, the radiation source 20 may be a treatment radiation source, in which cases, the imager 24 may be an on-board imager.

It should be noted that the system 10 is not limited to the configuration described above, and that the system 10 may have other configurations in other embodiments. For example, in other embodiments, the system 10 may have a different shape. In other embodiments, the radiation source 20 of the system 10 may have different ranges of motions and/or degrees of freedom. For example, in other embodiments, the radiation source 20 may be rotatable about the patient 28 completely through a 360° range, or partially through a range that is less than 360°. Also, in other embodiments, the radiation source 20 is translatable relative to the patient 28. In some embodiments, the system 10 may be a CT system. In other embodiments, the system 10 may be a radiation treatment system. In such cases, the radiation source 20 is not limited to delivering diagnostic energy in the form of x-ray, and may deliver treatment energy for treating a patient. Also, in some embodiments, the gantry 12 of the system 10 may cooperate with the patient support 14 to achieve a spiral motion. For example, the gantry 12 may rotate while the patient support 14 is being translated along its longitudinal axis.

During a scan to acquire x-ray image data (projection data), the gantry 12 rotates about the patient 28 at different gantry angles, so that the radiation source 20 and the imager 24 may be used to obtain images at different gantry angles. As the system 10 is operated to obtain images at different gantry angles, the patient 28 is breathing. Thus, the resulting images at different gantry angles may correspond to different phases of a breathing cycle for the patient 28. After the scan is completed, or while the scan is continued to obtain additional projection images, the generated projection images at different gantry angles are stored, e.g., in a memory, and the projection images are processed to sort the images so that images that correspond to a same phase or a same phase range of a breathing cycle are binned (e.g., associated with each other). The binned images for a specific phase of a respiratory cycle can then be used to reconstruct a digital volumetric image for that phase.

As shown in the figure, the system 10 may optionally further include a patient position determining system 70 that includes a camera 80 and a marker block 82 having a plurality of markers 84. The patient position determining system 70 is configured to determine amplitude and/or phase of a physiological movement of the patient 28. During use, the marker block 82 may be placed on the patient's chest, and the camera 80 is then used to view the markers 84 on the marker block 82. During a respiratory cycle, the chest of the patient 28 will move up and down, and the marker block 82 will move correspondingly. Because the relative positions among the markers 84 on the block 82 are known and pre-determined, by using this information, the processor 54 may be configured to process the image(s) from the camera 80 to determine a position of the marker block 82 relative to some arbitrary reference coordinate. By continuously tracking the position of the marker block 82, the processor 54 may determine the breathing amplitudes and/or phases of the breathing cycle that the patient 28 is going through. The determined amplitudes and/or phases may then be later used by the processor 54 to sort the images so that different sets of images correspond with respective phases or phase ranges of the breathing cycle, as similarly discussed.

Alternatively, the camera 80 may be configured to use other things as marker(s), such as a patient's clothes, a physiological feature of the patient 28, etc. Thus, in other embodiments, the marker block 82 may be optional, and the patient position determining system 70 may not include any marker block 82. Examples of a patient position determining system include Varian's RPM product, which is capable of recording amplitudes and phases of a breathing signal along with image data. In other embodiments, the patient position determining system 70 may be other systems known in the art, such as a strain-gauge for measuring chest expansion, spirometer, etc., as long as the system can determine a state of the patient's 28 motion (e.g., breathing, cardiac motion, etc.). Also, in further embodiments, the patient position determining system 70 may use internal fiducial(s), such as implanted marker(s), anatomical feature(s), etc., for determining a state of a physiological cycle.

Figure 2:
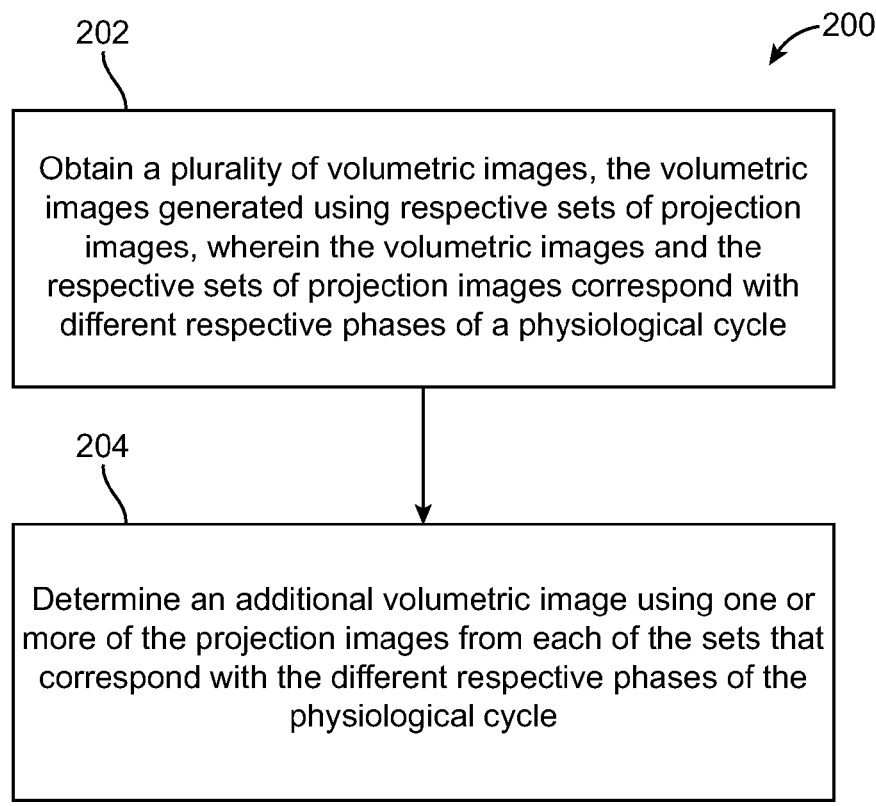
FIG. 2 illustrates a method of obtaining one or more volumetric images in accordance with some embodiments.

FIG. 2 illustrates a method 200 for determining a volumetric image in accordance with some embodiments. The method 200 will be described with reference to the system 10 of FIG. 1. However, it should be understood that the method 200 may be performed using other systems in other embodiments.

Figure 3:
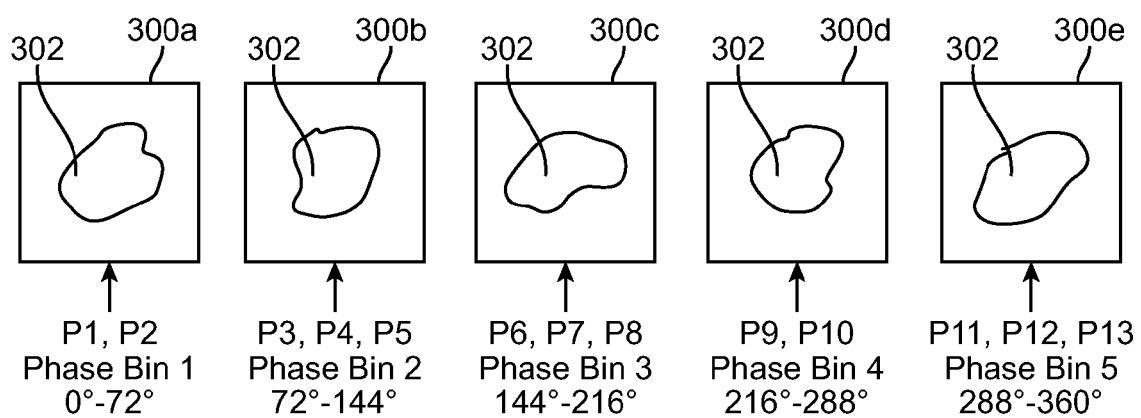
FIG. 3 illustrates different volumetric images obtained using the system of FIG. 1 in accordance with some embodiments.

First, a plurality of volumetric images are obtained (Item 202). In the illustrated embodiments, the volumetric images are generated using respective sets of projection images, wherein the volumetric images and the respective sets of projection images correspond with different respective phases of a physiological cycle. FIG. 3 illustrates an example of a sequence of volumetric images 300a-300e, which may be an example of the plurality of volumetric images referenced in Item 202. Each volumetric image 300 includes an image of a body part 302. The volumetric images 300a-300e may be displayed in a sequence to form a video, so that a user can see how the body part 302 moves in a physiological cycle (e.g., respiratory cycle).

In the illustrated example, volumetric image 300a is generated using projection images P1, P2, volumetric image 300b is generated using projection images P3, P4, P5, volumetric image 300c is generated using projection images P6, P7, P8, volumetric image 300d is generated using projection images P9, P10, and volumetric image 300e is generated using projection images P11, P12, P13. Although two or three projection images are illustrated as being used to form a volumetric image, it should be understood that this is for illustrative purpose, and that a volumetric image may be formed using more than three projection images.

The projection images P1-P13 may be generated using the system 10 (or another imaging system). While the projection images P1-P13 are being generated, the patient is breathing. As a result, the projection images P1-P13 may correspond to different respective phases of a breathing cycle. In the illustrated embodiments, for each projection image that is obtained while the patient is at a certain phase of a respiratory cycle, the processor 54 receives signals from the patient position monitoring system that indicate the corresponding phase, and the processor 54 associates the image with the corresponding phase. The images and their respective associated phases may be stored in a non-transitory medium for later processing. After the projection images P1-P13 are generated, they may be sorted so that different projection images that are within a certain phase range are grouped. In the illustrated example, projection images P1, P2 are grouped into phase bin 1, projection images P3, P4, P5 are grouped into phase bin 2, projection images P6, P7, P8 are grouped into phase bin 3, projection images P9, P10 are grouped into phase bin 4, and projection images P11, P12, P13 are grouped into phase bin 5.

Figure 4:
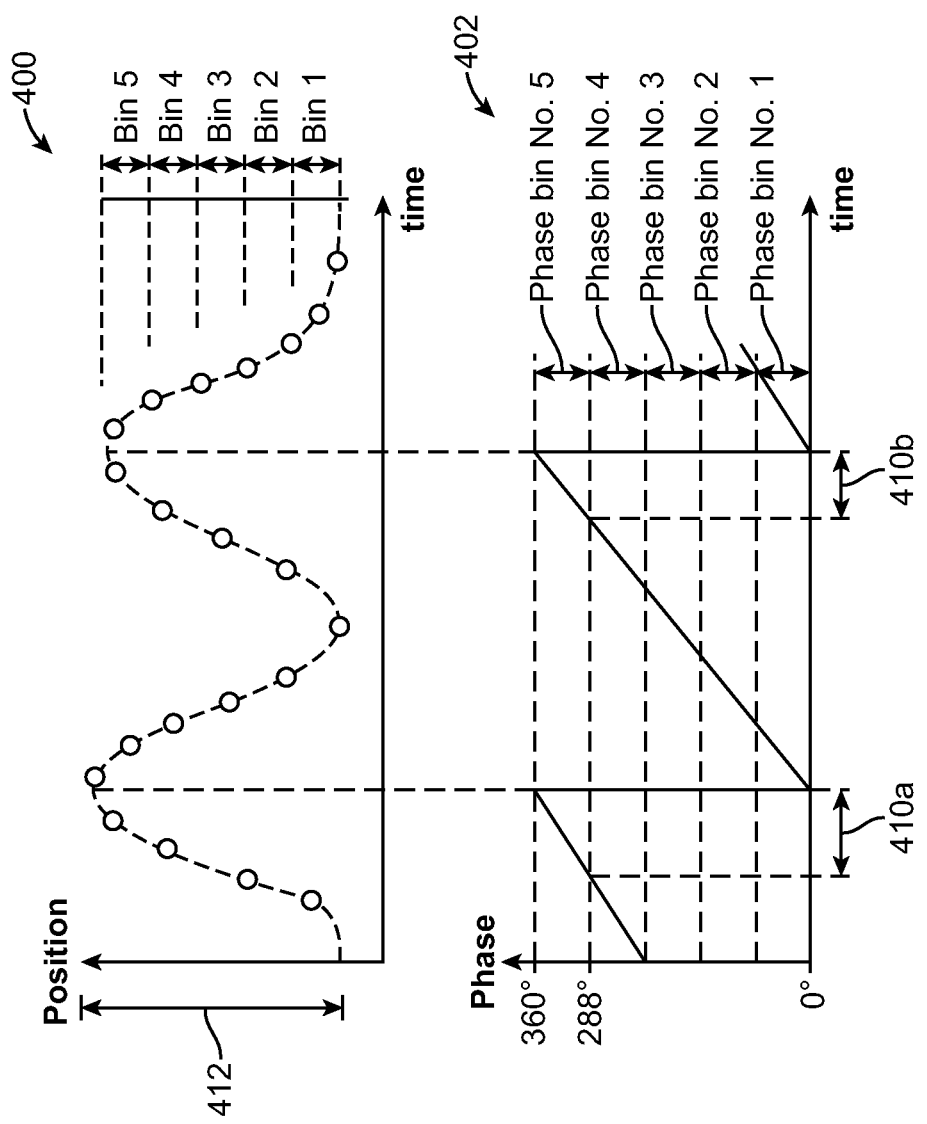
FIG. 4 illustrates a phase diagram aligned with a corresponding amplitude diagram in accordance with some embodiments.

In the illustrated embodiments, signals from the patient position monitoring system 70 may be used by the processor 54 to sort the projection images. In particular, while the imager 24 generates the projection images, the patient position monitoring system 70 is used to obtain position signals (e.g., in a form of camera images). The camera images are processed by the processor 54, which determines breathing amplitudes. FIG. 4 illustrates an example of the determined breathing amplitudes of respiratory cycles plotted against time to form an amplitude curve 400. In some embodiments, the processor 54 may also use the determined breathing amplitudes to determine phases of a respiratory cycle. A phase of a respiratory cycle represents a degree of completeness of the respiratory cycle. FIG. 4 also illustrates a phase curve 402 having phase values plotted against time, wherein the phase curve 402 corresponds with the amplitude curve 400. In the illustrated example, a phase value of 0° (and 360°) represents a peak of an inhale state, and the phase value varies linearly between 0° and 360° in a physiological cycle.

The examples of the phase bins 1-5 described previously are also shown in the figure. Phase bin 1 is for a phase range of, e.g., 0°-72°, phase bin 2 is for a phase range of, e.g., 72°-144°, phase bin 3 is for a phase range of, e.g., 144°-216°, phase bin 4 is for a phase range of, e.g., 216°-288°, and phase bin 5 is for a phase range of, e.g., 288°-360°. In such example, all images with phase values from 0°-72°, 72°-144°, 144°-216°, 216°-288°, and 288°-360° will be grouped by the processor 54 into phase bins Nos. 1-5, respectively. For examples, projection image P1 may be obtained when the patient is at phase=45°, and projection image P2 may be obtained when the patient is at phase=53°. As a result, both of these projection images P1, P2 may be sorted by the processor 54 so that they are grouped into phase bin 1, which covers a phase range of 0°-72°. Similarly, the projection images P3, P4, P5 are generated when the patient is anywhere from 72°-144° in phase of a respiratory cycle, and thus, they are binned into phase bin 2. The projection images P6, P7, P8 are generated when the patient is anywhere from 144°-216° in phase of a respiratory cycle, and thus, they are binned into phase bin 3. The projection images P9, P10 are generated when the patient is anywhere from 216°-228° in phase of a respiratory cycle, and thus, they are binned into phase bin 4. The projection images P11, P12, P13 are generated when the patient is anywhere from 288°-360° in phase of a respiratory cycle, and thus, they are binned into phase bin 5. The projection images P11, P12, P13 may be generated during time durations 410a, 410b, for example, as shown in FIG. 4. Note that the duration of the time periods 410a, 410b in the example are not necessarily equal, and that they may be different, depending on the breathing pattern of the patient 28.

It should be noted that the number of phase bins is not limited to five, and that in other embodiments, the number of phase bins for sorting the projection images may be less than five, or more than five. Also, instead of having equal sizes, in some embodiments, the phase ranges in the respective bins may be different from each other. In other embodiments, the phase ranges of the respective bins may overlap. For example, in some embodiments, phase bin 2 may be from 36° to 180°, phase bin 3 may be from 108° to 252°, phase bin 4 may be from 180° to 324°, etc. In such cases, the phase bins may provide double coverage. In other cases, the coverage may be smaller or greater than double (two times). In some embodiments, the number of bins may be user prescribed. For example, a user may prescribe a certain number of phase bins (e.g., 5 phase bins) using the input device 58. Also, in some embodiments, the processor 54 may generate each volumetric image 300 using a subset of the projection images in each phase bin (set), so that not all of the projection images in each set are used for the construction of the volumetric image 300. In other embodiments, the processor 54 may use all of the projection images in each set to construct the volumetric image 300.

In some embodiments, the act of obtaining the volumetric images may be performed by a processor (e.g., processor 54) receiving the volumetric images. In other embodiments, the act of obtaining the volumetric images may be performed by a processor (e.g., processor 54), which receives projection images, sorts the projection images into different sets (bins) based on their respective phases, and reconstruct the volumetric images using the respective sets of sorted projection images. In some embodiments, the projection images and/or the volumetric images may be stored in a non-transitory medium for processing and/or retrieval later. Additionally, in some embodiments, the projection images and/or the volumetric images may be displayed in a screen (e.g., screen 56) for viewing by a user.

In the illustrated embodiments, the grouping of the projection images P is described as being based on phase. In other embodiments, the grouping of the projection images P may be based on amplitude of a respiratory cycle. For example, in some embodiments, the amplitude range 412 in a respiratory cycle may be divided into a number of amplitude bins (e.g., five amplitude bins, as shown in the figure). In such cases, projection images P that are generated when the amplitude is within the amplitude range of an amplitude bin are grouped into that bin. In other embodiments, the number of amplitude bins may be fewer than five, or more than five. Also, instead of having equal sizes, in some embodiments, the ranges (e.g., phase ranges, amplitude ranges, etc.) in the respective bins (e.g., phase bins, amplitude bins, etc.) may be different from each other. In further embodiments, the ranges in the respective bins (e.g., phase bins, amplitude bins, etc.) may overlap.

Returning to FIG. 2, next, an additional volumetric image is determined using one or more of the projection images from each of the sets that correspond with the different respective phases of the physiological cycle (Item 204). In some embodiments, the act of determining the additional volumetric image may be performed using a processor (e.g., the processor 54). For example, an additional volumetric image for bin 1 may be determined using projection images from bin 1, projection images from bin 2, projection images from bin 3, etc.

Figure 5:
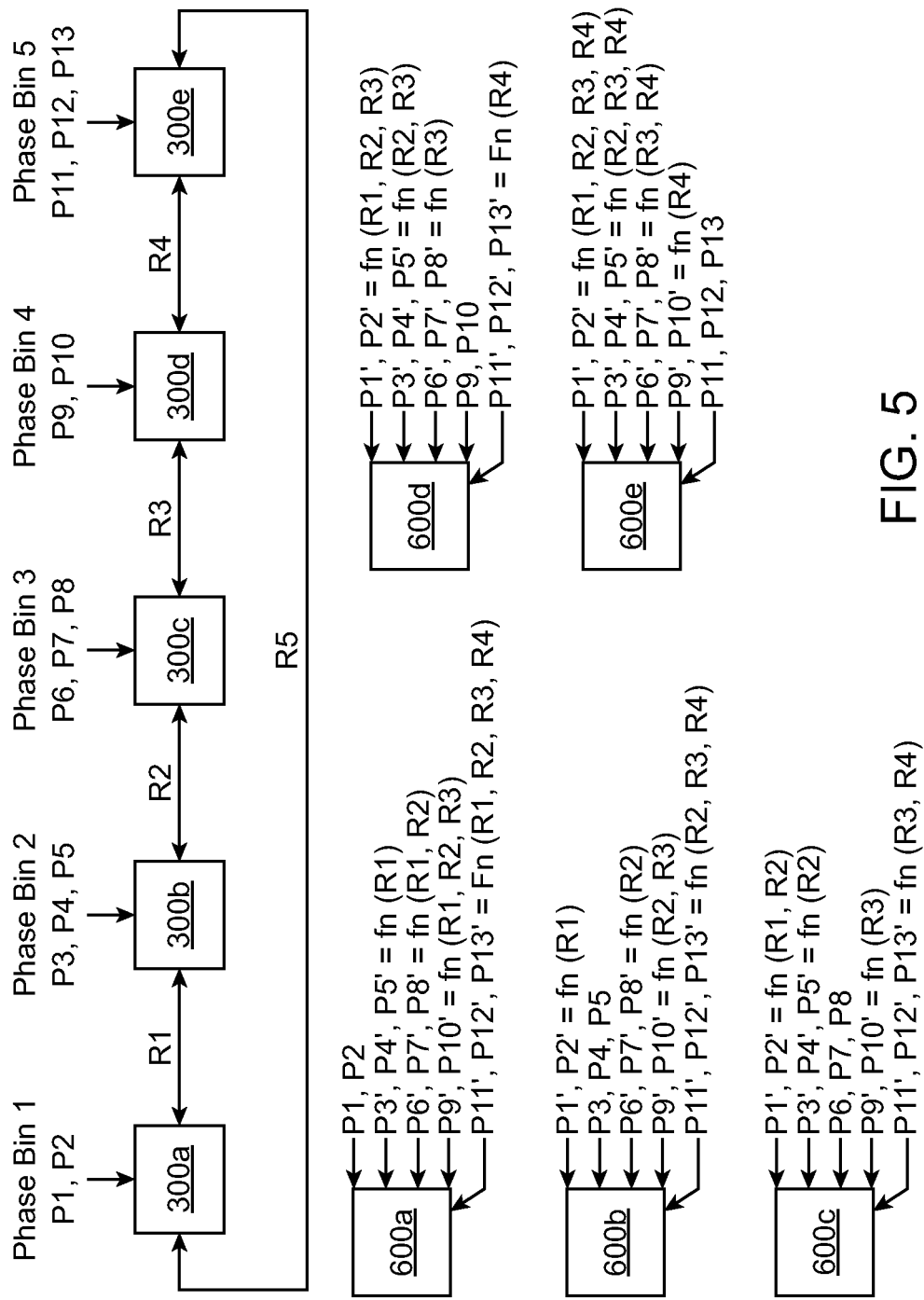
FIG. 5 illustrates a technique for obtaining a volumetric image in accordance with some embodiments.

FIG. 5 illustrates a technique of determining a volumetric image based on projection images from different bins using image registration in some embodiments. The technique of FIG. 5 may be an example of the Item 204 in the method 200. In the illustrated embodiments, each of the initial volumetric images 300a-300e is registered with its adjacent volumetric image. Thus, an image registration R1 may be determined between volumetric images 300a, 300b, an image registration R2 may be determined between volumetric images 300b, 300c, an image registration R3 may be determined between volumetric images 300c, 300d, an image registration R4 may be determined between volumetric images 300d, 300e, and an image registration R5 may be determined between volumetric images 300e, 300a. In some embodiments, each image registration R may be a deformation registration that represents a change between two adjacent volumetric images 300. For example, in some embodiments, the deformation registration may include a plurality of vectors that represent how different parts in one volumetric image 300 are "deformed" to reach the configuration (e.g., size, shape, and/or position) of the corresponding parts in the adjacent volumetric image 300. In some embodiments, the determining of the registrations R may be performed by a processor (e.g., processor 54). Also, in some embodiments, the data regarding the registrations R may be stored in a non-transitory medium for later retrieval and/or processing. In further embodiments, the data regarding the registrations R may also be displayed in a screen (e.g., screen 56) for viewing by a user.

In the illustrated embodiments, a new volumetric image may be determined using the determined registration(s) R. As shown in the figure, a new volumetric image 600a, which corresponds with the same phase or phase range of the volumetric image 300a, may be determined using projection images from other phase bins (i.e., phase bins 2-5) and the determined registrations R. In particular, because the volumetric image 600a is for the same phase or phase bin as that of volumetric image 300a, the same projection images P1, P2 may be used to construct the additional volumetric image 600a without any modification. On the other hand, because the projection images P3, P4, P5 are from a different phase bin (phase bin 2), in order to use these projection images for constructing the volumetric image 600a, these projection images are modified into projection images P3', P4', P5' using the registration R1. The modification is possible because the registration R1 between the volumetric image 600a and 600b provides information on how the two volumetric images 600a, 600b differ from each other. Thus, the registration information may be used to obtain modified projection images P3', P4', P5' (which correspond with the same gantry angles at which projection images P3, P4, P5 were generated, respectively) as if they were generated for phase bin 1.

In some embodiments, the volumetric image 300b may be transformed by a deformation using registration R1 resulting in a deformed volumetric image to reach the configuration (e.g., size, shape, and/or position) of the volumetric image 300a. A forward projection of the deformed volumetric image at the same gantry angles for the respective projection images P3, P4, P5, may then be performed to generate the modified projection images P3', P4', P5'. The modified projection images P3', P4', P5' are then used to form the new volumetric image 600a. For example, the projection images P3', P4', P5' may be the only images used to construct the volumetric image 600a. Alternatively, the projection images P3', P4', P5' may be used with other projection images (e.g., projection images from the phase bin 1, and/or projection images from other phase bin(s)) to form the new volumetric image 600a. In other embodiments, the registration R1 may be directly incorporated in the reconstruction of the volumetric image 600a without performing the intermediate act of determining modified projection images P3', P4', P5' (which may obviate performing a forward projection and a back projection). In either one of the techniques, the original projection images P3, P4, P5 may be considered as being "used" to determine the new (additional) volumetric image 600a.

Similarly, because the projection images P6, P7, P8 are from a different phase bin (phase bin 3), in order to use these projection images for constructing the volumetric image 600a, these projection images are modified into projection images P6', P7', P8' using the registrations R1, R2. Note that both registrations R1, R2 are used for modifying the projection images P6, P7, P8 because the registration R2 provides information on how the volumetric image 300c is different from the volumetric image 300b, but not how the volumetric image 300c is different from the volumetric image 300a. Thus, in order to have sufficient information regarding how the volumetric image 300c is different from (or to be transformed to) the volumetric image 300a, or vice versa, both registrations R1, R2 are used.

Similarly, because the projection images P9, P10 are from a different phase bin (phase bin 4), in order to use these projection images for constructing the volumetric image 600a, these projection images are modified into projection images P9', P10' using the registrations R1, R2, R3. Note that the registrations R1, R2, R3 are used for modifying the projection images P9, P10 because these three registrations provide sufficient information regarding how the volumetric image 300d is different from the volumetric image 300a. Alternatively, instead of using the registrations R1, R2, R3 for modifying the projection images P9, P10, the registrations R4, R5 may be used. This is because the combination of registrations R4, R5 also provides information on how the volumetric image 300d is different from (or to be transformed to) the volumetric image 300a, or vice versa.

Similarly, because the projection images P11, P12, P13 are from a different phase bin (phase bin 5), in order to use these projection images for constructing the volumetric image 600a, these projection images are modified into projection images P11', P12', P13' using the registrations R1, R2, R3, R4. Note that the registrations R1, R2, R3, R4 are used for modifying the projection images P11, P12, P13 because these four registrations provide sufficient information regarding how the volumetric image 300e is different from the volumetric image 300a. Alternatively, instead of using the registrations R1, R2, R3, R4 for modifying the projection images P11, P12, P13 the registration R5 may be used. This is because the registration R5 also provides information on how the volumetric image 300e is different from (or to be transformed to) the volumetric image 300a, or vice versa.

As illustrated in the above example, the new volumetric image 600a for phase bin 1 is determined using the projection images P1, P2 that are associated with phase bin 1, and the modified projection images P3'-P13' from other phase bins 2-5. In some embodiments, such technique allows all of the projection images P1-P13 to be used for determining the volumetric image 600a. In other embodiments, instead of using all of the projection images P1-P13, the determination of the volumetric image 600a may be achieved by constructing the volumetric image 600a using one or more of the projection images, that are less than all of the projection images, from each of the sets (phase bins).

In some embodiments, the same technique may be applied to determine additional volumetric images for other phase bins (i.e., any or all of phase bins 2-5). For example, as shown in the figure, in other embodiments, another new volumetric image 600b that corresponds with phase bin 2 may be constructed using the original projection images P3, P4, P5 associated with the phase bin 2, and modified projection images P1', P2', and P6'-P13'. In the illustrated examples, modified projection images P1', P2' are obtained by modifying projection images P1, P2 using registration R1, which provides information on how the volumetric image 300b is different from (or to be transformed to) the volumetric image 300a, or vice versa. Also, the modified projection images P6', P7', P8' are obtained by modifying projection images P6, P7, P8 using registration R2, which provides information on how the volumetric image 300b is different from (or to be transformed to) the volumetric image 300c, or vice versa. The modified projection images P9', P10' are obtained by modifying projection images P9, P10 using the combination of registrations R2, R3, which provides information on how the volumetric image 300b is different from (or to be transformed to) the volumetric image 300d, or vice versa. Similarly, the modified projection images P11', P12', P13' are obtained by modifying projection images P11, P12, P13 using the combination of registrations R2, R3, R4, which provides information on how the volumetric image 300b is different from (or to be transformed to) the volumetric image 300e, or vice versa. Alternatively, the projection images P11, P12, P13 may be modified using the combination of registrations R1, R5, which also provides information on how the volumetric image 300b is different from (or to be transformed to) the volumetric image 300e, or vice versa.

The same technique may be applied to determine new volumetric images 600c, 600d, 600e. The resulting sequence of new volumetric images 600a-600e may be considered modified or improved version of the initial volumetric images 300a-300e, respectively. As illustrated in the example, each of the volumetric images 600 in the sequence is determined (e.g., constructed) using all of the projection images P1-P13 from the different phase bins 1-5. This is advantageous because it allows a full dose usage in the determination of the sequence of volumetric images. In other embodiments, one or more of the new volumetric images 600a-600e may be determined using one or more of the projection images, but not all, from each phase bin.

Also, in other embodiments, the projection images may be binned into different respective bins that are amplitude bins (instead of phase bins). For example, if a total amplitude range for a breathing cycle is 10 mm, then 5 amplitude bins may be prescribed that cover amplitude ranges 1-2 mm, 2-4 mm, 4-6 mm, 6-8 mm, and 8-10 mm, respectively. In such cases, projection images that are generated when the breathing amplitudes are within a certain amplitude range will be binned into the corresponding amplitude bin. In some embodiments, each of the volumetric images 600 in the sequence may be determined (e.g., constructed) using all of the projection images P1-P13 from the different amplitude bins. In other embodiments, one or more of the new volumetric images 600a-600e may be determined using one or more of the projection images, but not all, from each amplitude bin.

Also, instead of having equal sizes, in some embodiments, the amplitude ranges in the respective bins may be different from each other. In other embodiments, the amplitude ranges of the respective bins may overlap.

It should be noted that the types of bins that may be used with the method 200 are not limited to the phase bins and amplitude bins described in the above examples, and that other types of bins may be used in other embodiments.

In the above embodiments, the new volumetric images 600 are described as being for the same phases or amplitudes for the initial volumetric images 300. In other embodiments, any of the new volumetric images 600 may be for a phase or amplitude that is different from those for the initial volumetric images 300. Following the above example, a new volumetric image 600 may be constructed for a phase range (bin) that is from, e.g., 36°-108° (i.e., between the phase ranges for phase bins 1 and 2). In such cases, the new volumetric image 600 may be constructed using interpolation techniques on the registrations R. It should be noted that a new volumetric image 600 may be constructed for any arbitrary phase or phase ranges (or for any arbitrary amplitude or amplitude ranges) of a physiological cycle using interpolation techniques. Also, in some embodiments, via the same interpolation techniques, the processor may perform a deformation specifically for any projection image in order to consider residual motion within a bin.

In some embodiments, the modifying of the projection images may be performed using a processor (e.g., the processor 54). In some embodiments, the registrations R may be represented by respective matrices. In other embodiments, such as free form deformation, the representation may be more complex (e.g. involving b-splines). Also, in some embodiments, when two or more registrations R are involved in modifying a projection image, the processor may be configured to combine the registrations R. In some embodiments, the combination of registrations R may be a mathematical concatenation. In some embodiments, the processor may be configured to iteratively perform the multiplication or concatenation. For example, to obtain a combined matrix for modifying the projection images P11, P12, P13 to construct the volumetric image 600a, the processor may be configured to calculate a combined matrix by multiplying R1 with R2, and then with R3, and then with R4. This results in the projection images being sequentially modified as additional registration R is being applied.

In the above embodiments, registrations R between adjacent images are combined. In other embodiments, the processor (e.g., processor 54) may be configured to replace each combination of registrations by the resulting deformation registration of the respective volumetric images 300 (which are not adjacent). For example, the combined registration of R1, R2 may be replaced by the deformation registration between volumetric images 300a, 300c (wherein the volumetric image 300c is not adjacent to the volumetric image 300a).

Also, in the above embodiments, modified projection images are generated using registration(s) R, and the modified projection images are then used to determine the new volumetric image 600. In other embodiments, the determination of the modified projection images is not required. For example, in other embodiments, the processor (e.g., the processor 54) may directly incorporate registration(s) R in the reconstruction of the new volumetric image(s) 600 without performing the intermediate act of determining modified projection images (which may obviate performing a forward projection and a back projection). In some embodiments, because the determination of the additional volumetric image 600 for a given bin involves using a volumetric image 300 for another bin, and because the volumetric image 300 for the other bin is based on projection images for that other bin, it may be said that the determination of the additional volumetric image 600 involves using projection images from other bin.

Figure 6:
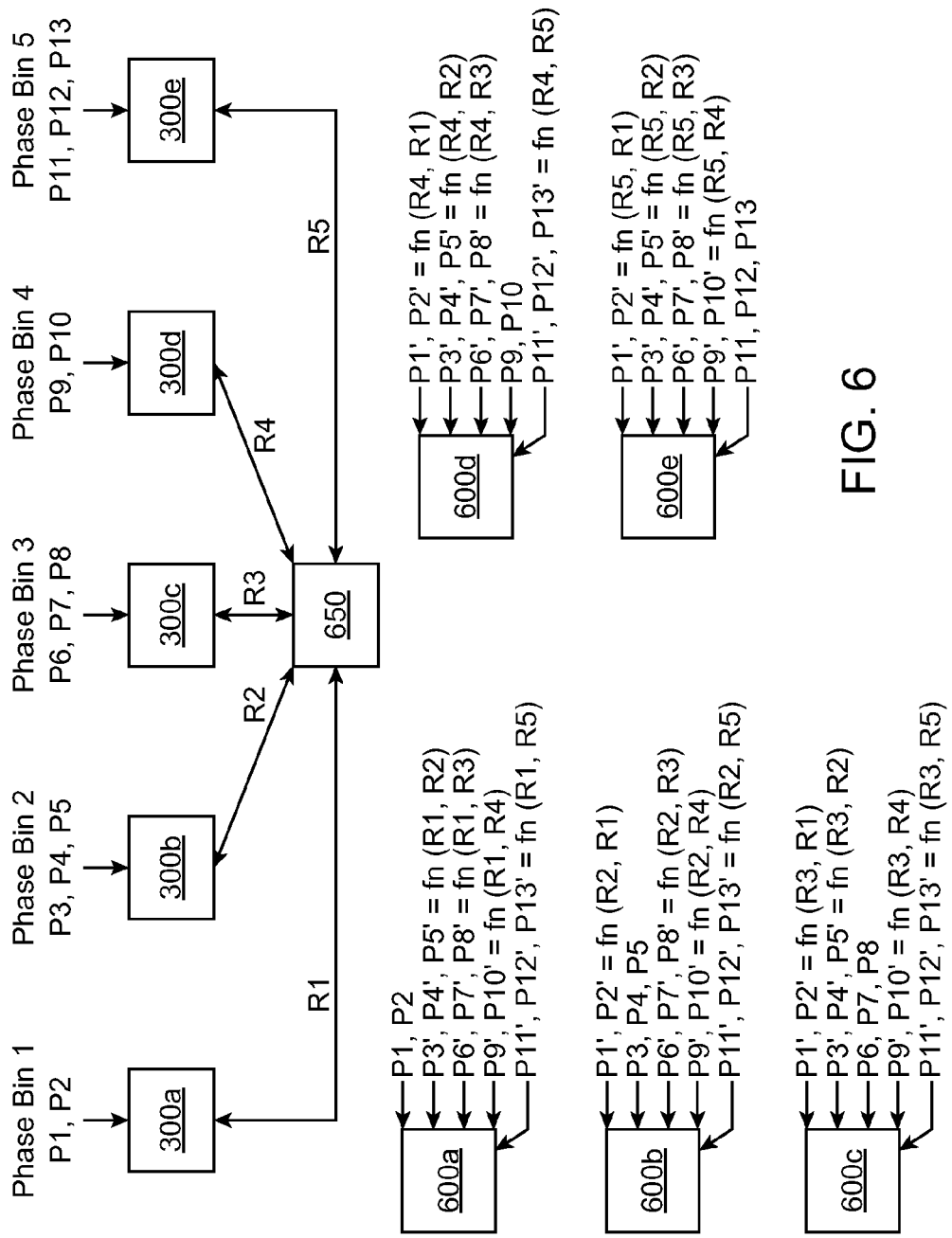
FIG. 6 illustrates another technique for obtaining a volumetric image in accordance with other embodiments.

In the above embodiments, each of the registrations R is obtained by processing two adjacent volumetric images 300 (e.g., volumetric images that are adjacent to each other in bin order). In other embodiments, one or more of the registrations R may be obtained by processing each of the volumetric images 300 with a reference image. FIG. 6 illustrates a technique of determining a volumetric image that involves using image registration in other embodiments. The technique of FIG. 6 may be another example of the Item 204 in the method 200. In the illustrated embodiments, each of the initial volumetric images 300a-300e is registered with a reference volumetric image 650. Thus, an image registration R1 may be determined between volumetric images 300a, 650, an image registration R2 may be determined between volumetric images 300b, 650, an image registration R3 may be determined between volumetric images 300c, 650, an image registration R4 may be determined between volumetric images 300d, 650, and an image registration R5 may be determined between volumetric images 300e, 650. In some embodiments, each image registration R may be a deformation registration that represents a change between two volumetric images. For example, in some embodiments, the deformation registration may include a plurality of vectors that represent how different parts in one volumetric image 300 are "deformed" to reach the configuration (e.g., size, shape, and/or position) of the corresponding parts in the reference image 650, or vice versa. In some embodiments, the determining of the registrations R may be performed by a processor (e.g., processor 54). Also, in some embodiments, the data regarding the registrations R may be stored in a non-transitory medium for later retrieval and/or processing. In further embodiments, the data regarding the registrations R may also be displayed in a screen (e.g., screen 56) for viewing by a user.

In some embodiments, the reference image 650 may be a volumetric image that was pre-determined, such as from a previous imaging session. In other embodiments, the reference image 650 may be any one of the volumetric images 300a-300e. Also, in some embodiments, the reference image 650 may be arbitrarily selected from the volumetric images 300a-300e. In other embodiments, the reference image 650 may be selected based on certain criteria.

In the illustrated embodiments, a new volumetric image may be determined using the determined registration(s) R. As shown in the figure, a new volumetric image 600a, which corresponds with the same phase or phase range of the volumetric image 300a, may be determined using projection images from other phase bins (i.e., phase bins 2-5) and the determined registrations R. In particular, because the volumetric image 600a is for the same phase or phase bin as that of volumetric image 300a, the same projection images P1, P2 may be used to construct the additional volumetric image 600a without any modification. On the other hand, because the projection images P3, P4, P5 are from a different phase bin (phase bin 2), in order to use these projection images for constructing the volumetric image 600a, these projection images are modified into projection images P3', P4', P5' using the registrations R1, R2. Note that both registrations R1, R2 are used for modifying the projection images P3, P4, P5 because the registration R2 provides information on how the volumetric image 300b is different from the reference volumetric image 650, but not how the reference image 650 is different from the volumetric image 300a. Thus, in order to have sufficient information regarding how the volumetric image 300b is different from (or to be transformed to) the volumetric image 300a, or vice versa, both registrations R1, R2 are used.

Similarly, because the projection images P6, P7, P8 are from a different phase bin (phase bin 3), in order to use these projection images for constructing the volumetric image 600a, these projection images are modified into projection images P6', P7', P8' using the registrations R1, R3. Note that both registrations R1, R3 are used for modifying the projection images P6, P7, P8 because the registration R3 provides information on how the volumetric image 300c is different from the reference volumetric image 650, but not how the reference image 650 is different from the volumetric image 300a. Thus, in order to have sufficient information regarding how the volumetric image 300c is different from (or to be transformed to) the volumetric image 300a, or vice versa, both registrations R1, R3 are used.

Similarly, because the projection images P9, P10 are from a different phase bin (phase bin 4), in order to use these projection images for constructing the volumetric image 600a, these projection images are modified into projection images P9', P10' using the registrations R1, R4. Note that both registrations R1, R4 are used for modifying the projection images P9, P10 because the registration R4 provides information on how the volumetric image 300d is different from the reference volumetric image 650, but not how the reference image 650 is different from the volumetric image 300a. Thus, in order to have sufficient information regarding how the volumetric image 300d is different from (or to be transformed to) the volumetric image 300a, or vice versa, both registrations R1, R4 are used.

Similarly, because the projection images P11, P12, P13 are from a different phase bin (phase bin 5), in order to use these projection images for constructing the volumetric image 600a, these projection images are modified into projection images P11', P12', P13' using the registrations R1, R5. Note that both registrations R1, R5 are used for modifying the projection images P11, P12, P13 because the registration R5 provides information on how the volumetric image 300e is different from the reference volumetric image 650, but not how the reference image 650 is different from the volumetric image 300a. Thus, in order to have sufficient information regarding how the volumetric image 300e is different from (or to be transformed to) the volumetric image 300a, or vice versa, both registrations R1, R5 are used.

As illustrated in the above example, the new volumetric image 600a for phase bin 1 is determined using the projection images P1, P2 that are associated with phase bin 1, and the modified projection images P3'-P13' from other phase bins 2-5. In some embodiments, such technique allows all of the projection images P1-P13 to be used for determining the volumetric image 600a. In other embodiments, instead of using all of the projection images P1-P13, the determination of the volumetric image 600a may be achieved by constructing the volumetric image 600a using one or more of the projection images, that are less than all of the projection images, from each of the sets (phase bins).

In some embodiments, the same technique may be applied to determine additional volumetric images for other phase bins (i.e., any or all of phase bins 2-5). For example, as shown in the figure, in other embodiments, another new volumetric image 600b that corresponds with phase bin 2 may be constructed using the original projection images P3, P4, P5 associated with the phase bin 2, and modified projection images P1', P2', and P6'-P13'. In the illustrated examples, modified projection images P1', P2' are obtained by modifying projection images P1, P2 using a combination of the registrations R1, R2, which provides information on how the volumetric image 300b is different from (or to be transformed to) the volumetric image 300a, or vice versa. Also, the modified projection images P6', P7', P8' are obtained by modifying projection images P6, P7, P8 using a combination of the registrations R2, R3, which provides information on how the volumetric image 300c is different from (or to be transformed to) the volumetric image 300b, or vice versa. The modified projection images P9', P10' are obtained by modifying projection images P9, P10 using the combination of registrations R2, R4, which provides information on how the volumetric image 300d is different from (or to be transformed to) the volumetric image 300b, or vice versa. Similarly, the modified projection images P11', P12', P13' are obtained by modifying projection images P11, P12, P13 using the combination of registrations R2, R5, which provides information on how the volumetric image 300e is different from (or to be transformed to) the volumetric image 300b, or vice versa.

The same technique may be applied to determine new volumetric images 600c, 600d, 600e, as shown in the figure. The resulting sequence of new volumetric images 600a-600e may be considered modified or improved version of the initial volumetric images 300a-300e, respectively. As illustrated in the example, each of the volumetric images 600 in the sequence is determined (e.g., constructed) using all of the projection images P1-P13 from the different phase bins 1-5. This is advantageous because it allows a full dose usage in the determination of the sequence of volumetric images. In other embodiments, one or more of the new volumetric images 600a-600e may be determined using one or more of the projection images, but not all, from each set (e.g., phase bin).

In the above embodiments, modified projection images are generated using registration(s) R, and the modified projection images are then used to determine the new volumetric image 600. In other embodiments, the determination of the modified projection images is not required. For example, in other embodiments, the processor (e.g., the processor 54) may directly incorporate registration(s) R in the reconstruction of the new volumetric image(s) 600 without performing the intermediate act of determining modified projection images (which may obviate performing a forward projection and a back projection). In some embodiments, because the determination of the additional volumetric image 600 for a given bin involves using a volumetric image 300 for another bin, and because the volumetric image 300 for the other bin is based on projection images for that other bin, it may be said that the determination of the additional volumetric image 600 involves using projection images from other bin.

As illustrated in the above example, the embodiments of the technique of FIG. 6 are advantageous because the determination of each of the new volumetric images 600a-600e does not involve using more than two registrations R.

In the above embodiments (e.g., the embodiments of FIGS. 5 and 6), projection images P that spread across a complete phase range (e.g., 0°-360°) of the physiological cycle are used to construct each new volumetric image 600. In other embodiments, instead of using projection images P from a complete phase range, projection images P from at least 50% of the complete phase range of the physiological cycle may be used. For example, in other embodiments, the volumetric image 600a may be constructed using projection images from any three of the five phase bins 1-5 (e.g., from phase bins 1, 2, 3, or from phase bins 1, 3, 5, etc.). Also, in other embodiments, the volumetric image 600 may be constructed using projection images from only two of the sets (e.g., phase bins). For example, in other embodiments, the volumetric image 600 may be constructed from two projection images that are separated by a phase range that is at least 25% of a complete phase range for the physiological cycle. In further embodiments, instead of using projection images P from a complete phase range, projection images P from at least 90% of the complete phase range of the physiological cycle may be used.

Also, in other embodiments in which the bins are amplitude bins instead of phase bins, projection images P that spread across a total amplitude range of the physiological cycle may be used to construct each new volumetric image 600. In other embodiments, instead of using projection images P from the total amplitude range, projection images P from at least 50% of the total amplitude range of the physiological cycle may be used. For example, in other embodiments, the volumetric image 600a may be constructed using projection images from any three of the five amplitude bins 1-5. Also, in other embodiments, the volumetric image 600 may be constructed using projection images from only two of the sets (e.g., amplitude bins). For example, in other embodiments, the volumetric image 600 may be constructed from two projection images that are separated by an amplitude range that is at least 25% of a complete amplitude range for the physiological cycle. In further embodiments, instead of using projection images P from a complete amplitude range, projection images P from at least 90% of the complete amplitude range of the physiological cycle may be used.

It should be noted that the types of bins that may be used with the method 200 are not limited to the phase bins and amplitude bins described in the above examples, and that other types of bins may be used in other embodiments.

In some embodiments, the number of projection images from the corresponding bin (e.g., phase bin, amplitude bin, etc.) used by the processor to construct the volumetric image 600 may be more than the number of projection images from that bin to construct the initial volumetric image 300. In other embodiments, the number of projection images from the corresponding bin used by the processor to construct the volumetric image 600 may be equal to the number of projection images from that bin used to construct the initial volumetric image 300. In further embodiments, the number of projection images from the corresponding bin used by the processor to construct the volumetric image 600 may be less than the number of projection images from that bin used to construct the initial volumetric image 300.

Also, in other embodiments, instead of using all of the available projection images from all of the bins (e.g., phase bins, amplitude bins, etc.), a subset of all of the available projection image may be used to construct a new volumetric image 600. For example, in other embodiments, the volumetric image 600 may be determined using at least 50%, and more preferably at least 75%, and even more preferably at least 90%, of all of the projection images from all of the sets (e.g., phase bins, amplitude bins, etc.).

In addition, in one or more embodiments, the projection images at the different bins (e.g., phase bins, amplitude bins, etc.) may be all generated during an image session (e.g., in a day). For example, all of the projection images at the different bins may be generated while the patient 28 is at the patient support 14. In such cases, the projection images at the different bins may be generated in a sequence by rotating the gantry 12 to place the radiation source 20 at different gantry angles. In other embodiments, projection images at the different bins (e.g., different phase bins, amplitude bins, etc.) may be generated from different image sessions. For example, images generated while the patient's physiological cycle is anywhere from 0°-90° in phase taken in day 1 may be binned together with images for the same phase range (i.e., images generated while the patient's physiological cycle is anywhere from 0°-90°) taken in day 2. In some embodiments, such technique may be employed to reduce the radiation dose for the patient. For example, after obtaining some projection images (from previous imaging sessions that occurred in one or more days), the patient may be deemed as having predictable breathing motion, and it may not be necessary to obtain all of the projection images in any further imaging session(s) (e.g., in the current imaging session). In some embodiments, in the current imaging session, the radiation system 10 may be used to obtain a reduced number of projection images. In some cases, the reduced number of projection images may be used in conjunction with the previously obtained projection images to obtain new registrations R. In other cases, the previously created registrations R may be relied upon and re-used, and the projection images obtained in the current imaging session may be used as verification for the previously created registrations R.

Furthermore, in one or more embodiments, the screen 56 may display one or more information that is involved in the method 200. For example, in some embodiments, the screen 56 may display the original projection image(s) P, the modified projection image(s), the new volumetric image(s) 600, or combination of the foregoing. Also, in some embodiments, the new volumetric images 600 may be displayed in a sequence to form a video. Furthermore, one or more information that is involved in the method 200 may be stored in a non-transitory medium for later processing and/or for retrieval. For example, in some embodiments, a non-transitory medium may store the original projection image(s) P, the modified projection image(s), the new volumetric image(s) 600, etc. In some embodiments, the volumetric images 600 may be stored in a sequence in a form of a video.

Figure 7:
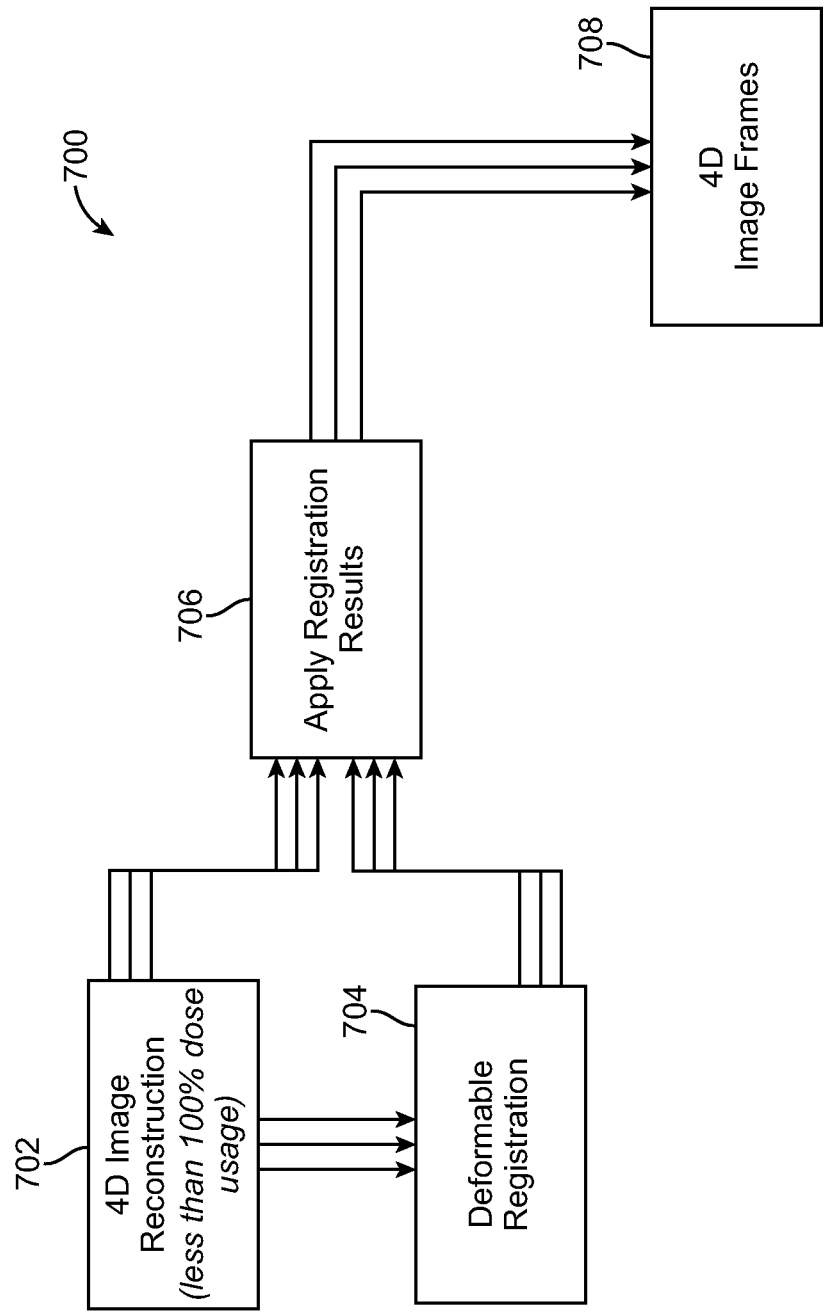
FIG. 7 illustrates a system for obtaining a volumetric image in accordance with some embodiments.

FIG. 7 illustrates a system 700 for performing the method 200 in accordance with some embodiments. The system 700 may be implemented using hardware, software, or combination of both. In some embodiments, the system 700 may be implemented using a processor (e.g., the processor 54), such as a general processor that is specifically configured to perform various functions (e.g., construction of volumetric image(s), deformation registration, modification of projection images, etc.) described herein. In other embodiments, the system 700 may be implemented using an ASIC. Also, in other embodiments, the system 700 may be implemented using a computer system. As shown in the figure, the system 700 includes a module 702 for obtaining volumetric image(s), a module 704 for determining registration between volumetric images, a module 706 for applying the determined registration to projection images, and a module 708 for determining new (additional) volumetric image(s). In some embodiments, the module 702 is configured (e.g., built and/or programmed) to perform the functions described with reference to Item 202 of method 200. For example, the module 702 may be configured to obtain the volumetric image(s) 300 by receive the volumetric image(s) 300. In other embodiments, the module 702 may be configured to obtain the volumetric image(s) 300 by performing image reconstruction using projection images. In some embodiments, the module 702 may be configured to use a subset (i.e., not all) of the projection images in each set (e.g., phase bins, amplitude bin, etc.) to construct a volumetric image 300. In other embodiments, the module 702 may be configured to use all of the projection images in each set to construct a volumetric image 300.

The module 704 is configured (e.g., built and/or programmed) to determine registration between volumetric images, such as between two adjacent volumetric images 300 like that described with reference to FIG. 5, or between a volumetric image 300 and a reference image 650 like that described with reference to FIG. 6. Thus, any of the functions regarding image registration (e.g., deformable registration) described with reference to the embodiments of FIG. 5 or 6 may be performed by the module 704. Also, in further embodiments, the module 704 may be configured to replace each combination of registrations by the resulting deformation registration of the respective volumetric images 300 (which are not adjacent). For example, the combined registration of R1, R2 may be replaced by the deformation registration between volumetric images 300a, 300c (wherein the volumetric image 300c is not adjacent to the volumetric image 300a).

The module 706 is configured (e.g., built and/or programmed) to apply the determined registration(s) R for modifying the projection images P, like that described with reference to the method 200. For example, in some embodiments, the module 706 may be configured to apply different registration(s) to the projection images in different sets, like that described with reference to the embodiments of FIG. 5 or 6, to thereby determine one or more modified projection images.

The module 708 is configured (e.g., built and/or programmed) to use the modified projection images to construct a new (additional) volumetric image, like that described with reference to Item 204 of the method 200, and the technique of FIG. 5 or 6. For example, in some embodiments, the module 708 may be configured to construct a volumetric image 600 for a particular bin (e.g., phase bin, amplitude bin, etc.) using projection images from that bin, as well as projection images from other bins. In some embodiments, the number of projection images from the corresponding bin used by the module 708 to construct the volumetric image 600 may be more than the number of projection images from that bin used by the module 702 to construct the initial volumetric image 300. In other embodiments, the number of projection images from the corresponding bin used by the module 708 to construct the volumetric image 600 may be equal to the number of projection images from that bin used by the module 702 to construct the initial volumetric image 300. Also, in other embodiments, the items 706, 708 may be combined, in which cases, the registration(s) R may be directly incorporated in the construction of a new (additional) volumetric volume without performing the intermediate act of modifying the projection images P.

In the above embodiments, the deformation registration has been described as being performed in an image space to estimate motion (motion vector fields). In other embodiments, the registration (e.g., deformation registration) may be performed in the projection image space. In such cases, the module 702 is not required, and the module 704 is configured to perform deformation registration(s) between projection images in the different respective bins (e.g., phase bins, amplitude bins, etc.). The registration(s) may then be used to determine a new volumetric image 600.

In some cases, 4D CT/CBCT images may have noise that is associated with an amount of dose delivered to the patient being imaged. For example, one objective of an imaging procedure for 4D CT/CBCT may be to use as little dose as possible. However, using less dose generally results in higher noise, and lower image quality. Although the noise may be reduced by increasing dose to patient, such technique may result in undesirable additional dose to the patient. Embodiments described herein may allow noise in 4D CT/CBCT images to be reduced without increasing dose to the patient. This is because by "borrowing" projection images from different sets (e.g., phase bins, amplitude bins, etc.), i.e., projection images generated when the patient is at different movement states, to construct the volumetric image for a certain movement state, the resulting volumetric image may have less noise without increasing dose to the patient.

In some embodiments, image(s) from different phase(s) of a motion cycle (respiratory, cardiac, or other) may be used to reduce noise for an image at a certain bin (e.g., phase bin, amplitude bin, etc.). In one implementation, the processor (e.g., processor 54) may be configured to deform an image (e.g., a reconstructed 3D image, or a slice of such 3D image) from another bin (source image) to look like the subject image. For example, the processor may perform a deformation registration between the source image and the subject image. Then the processor may perform a local-regional analysis to determine a similarity between the source image and the subject image. The processor then uses the determined similarity to determine a mixing weight, which is then applied by the processor to form a blended composite image using information from the source image and the subject image. Such technique is particularly beneficial if image at different bin does not change significantly, or if image at different bin may be accurately deformed to look like that in the subject image. In some cases, the deformed image may be significantly different from the subject image. In such cases, this technique may set the blending weight of the deformed image to 0. In some embodiments, the determination of the composite image may be performed by the processor using projection image data (i.e., before reconstruction of the volumetric image). In other embodiments, the processor may be configured to use the volumetric images to determine of the composite image. In some embodiments, the processor may use an image from an adjacent bin (e.g., phase bin, amplitude bin, etc.) in the above technique. In other embodiments, instead of the image at the adjacent bin, the processor may use other image(s) at other bin(s) that is not immediately adjacent to the image at the current bin. Also, in some embodiments, the processor may apply different weight factors when using images from different bins.

The above described technique may allow the subject image with relatively less noise to be obtained without increasing the dose to the patient. In some embodiments, the same technique may be applied for other subject images (i.e., images for different phases or phase ranges) to obtain a set of 4D CT/CBCT images that are improved versions of the original subject images. In some cases, the resulting 4D CT/CBCT data set with reduced noise may be compressed for storage.

In other embodiments, adjacent image slice(s) may be used to reduce noise for a particular image slice in a volumetric image. In one implementation, adjacent slice image is deformed to look like the subject image. Then local-regional analysis may be performed to determine similarity between the adjacent slice and the subject image. The determined similarity is then used to determine a mixing weight, which is then applied to form a blended composite image using the adjacent image slice and the subject image. Such technique is particularly beneficial if image at adjacent slice does not change significantly, or if image at adjacent slice may be accurately deformed to look like that in the subject image. In some cases the deformed adjacent slice may be significantly different from the subject image. In such cases, this technique may set the blending weight of the adjacent image slice to 0. In other embodiments, instead of adjacent image slice(s), the processor may be configured to use other image slice(s) that is not immediately next to the current slice. Also, in other embodiments, the processor may apply different weight factors when using different slice(s). For example, relatively less weight may be applied for slice that is further away in phase.

One technique to perform the local-regional analysis is to prescribe a multi-dimensional physical distance-to-agreement criteria, and an image value difference criteria. Such may be achieved by entering the criteria into a processor (e.g., through a user interface). For each point in the deformed image, the corresponding point in the subject image is identified by the processor. Then the processor computes the distance between that point and the nearest point in the image falling within the acceptable image value range. If the difference in position is within the distance-to-agreement criteria, and the difference in grey scale is within the tolerance, then the two points are considered "similar," and the two points are used to form a composite point. In some embodiments, the distance to agreement and image value criteria may be used by the processor to determine the mixing weight between the images. For example, the processor may be configured to average the grey scale of the two points. Alternatively, the processor may be configured to combine the grey scale of the two points with respective weight factors.

In other embodiments, the processor (e.g., the processor 54) may be configured to use different functions, e.g., continuous function, linear, exponential, etc., for local-regional analysis. For example, pixel in an image that is closer to the position of the pixel in the subject image may be given more weight by the processor in accordance with the function. Pixels in the image that are further away may have less weight (e.g., which decreases exponentially).

In other embodiments, local-regional analysis may be based on color instead of grey scale. For example, if the color of source pixel is within a certain prescribed tolerance from that of the subject pixel, then the processor may combine the two pixels.

In further embodiments, the local-regional analysis may be performed by the processor based on statistical data. For example, the distance-to-agreement and tolerance parameters may be statistical distributions that are considered by the processor when performing the local-regional analysis.

Figure 8:
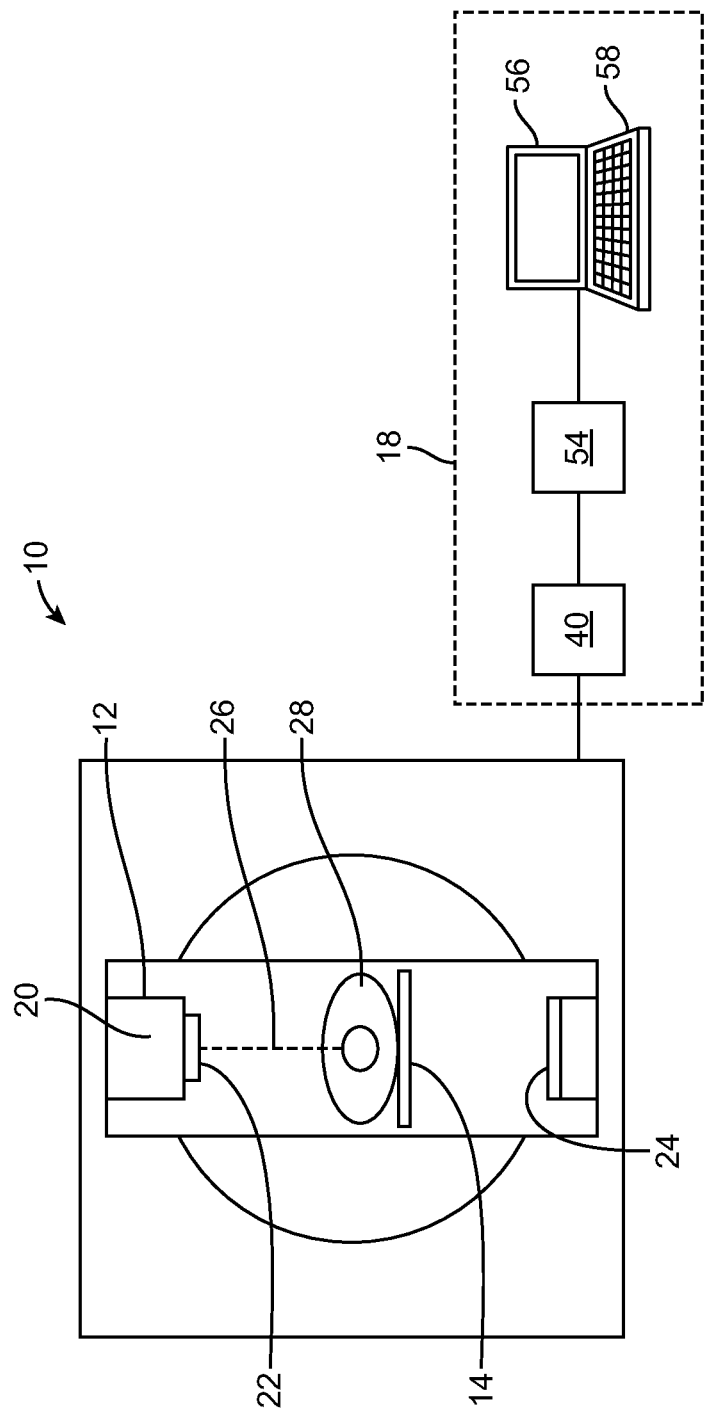
FIG. 8 illustrates another radiation system in accordance with other embodiments.

It should be noted that the system 10 that may be used in the method 200 is not limited to the example described previously. For example, in other embodiments, other imaging systems having different configurations may be used. For example, FIG. 8 illustrates another embodiment of the system 10 that may be used. The system 10 of FIG. 8 is a radiation system that includes a gantry 12, a patient support 14 for supporting a patient, and a control system 18 for controlling an operation of the gantry 12. The gantry 12 is in a form of an arm (e.g., a C-arm). The system 10 also includes a radiation source 20 that projects a beam 26 of radiation towards a patient 28 while the patient 28 is supported on support 14, and optionally a collimator system 22 for controlling a delivery of the radiation beam 26. The radiation source 20 can be configured to generate a cone beam, a fan beam, or other types of radiation beams in different embodiments. In the illustrated embodiments, the radiation source 20 is a diagnostic radiation source for providing diagnostic energy. In other embodiments, in addition to, or instead of, being a diagnostic radiation source, the radiation source 20 may be a treatment radiation source for providing treatment energy.

It should be noted that as used in this specification, the term "processor" (such as the processor 54) may refer to one or more processing units, such as one or more processors, which may or may not be a part of the system 10. Also, one or more functions described with reference to the processor 54 may be performed at least in part by the processor 54, completely by the processor 54, or completely by another processor (which may or may not be a part of the system 10). Also, the term "processor" may include one or more processing units, and may refer to any device that is capable of performing mathematical computation implemented using hardware and/or software.

In addition, it should be noted that the terms "first" and "second" (e.g., as in "first image" and "second image", "first phase", "second phase", etc.) refer to two things/items that are different or separate, and therefore, do not necessarily refer to the order in which the things are generated or arranged.

Also, the term "image" needs not be limited to an image that is displayed visually, and may refer to image data that is stored.

In addition, as used in this specification, the term "phase" may refer to a single phase or a range of phases. Similarly, the term "amplitude" may refer to a single amplitude or a range of amplitudes.

Furthermore, when a volumetric image is described as being determined "using" certain information (e.g., projection image(s), modified projection image(s), data (e.g., data regarding a registration, such as a matrix, a matrix value, a deformed volumetric image, a forward projection of a deformed image, etc.), etc.), it may refer to the information being used directly, or indirectly, to determine the volumetric image. Also, the information stated is not necessarily the only item that is "used" to determine the volumetric image. For example, with reference to the examples described in which projection images P are modified, and the modified projection images P' are then used to determine a volumetric image 600, it may be described that the volumetric image 600 is determined "using" a projection image P (because one of the projection images P is used in a process (in which the projection image P is modified) to determine the volumetric image 600).

Computer System Architecture

Figure 9:
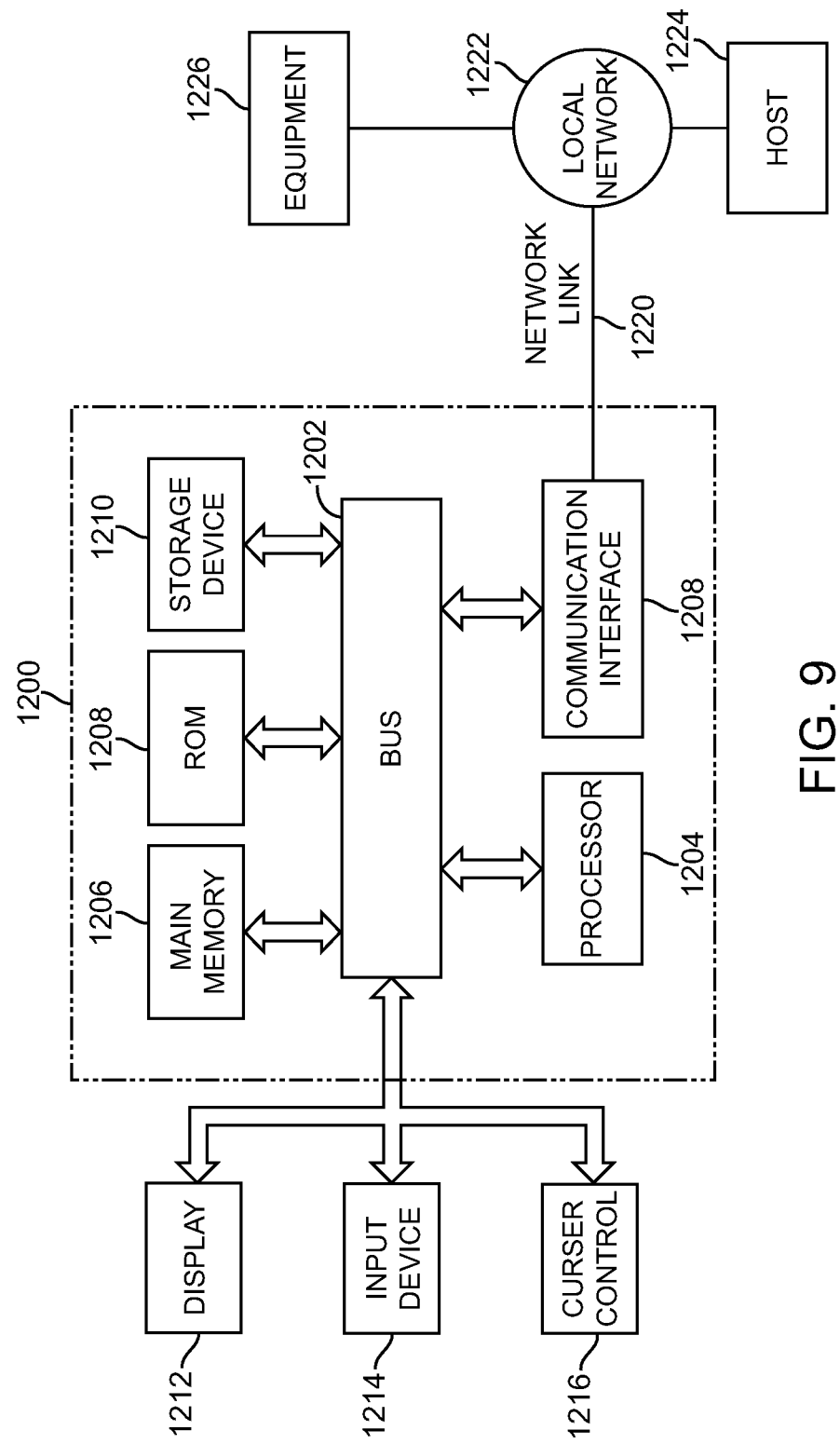
FIG. 9 is a block diagram of a computer system architecture, with which embodiments described herein may be implemented.

FIG. 9 is a block diagram that illustrates an embodiment of a computer system 1200 upon which embodiments described herein may be implemented. Computer system 1200 includes a bus 1202 or other communication mechanism for communicating information, and a processor 1204 coupled with the bus 1202 for processing information. The processor 1204 may be an example of the processor 54 of FIG. 1, or another processor that is used to perform various functions described herein. In some cases, the computer system 1200 may be used to implement the processor 54. The computer system 1200 also includes a main memory 1206, such as a random access memory (RAM) or other dynamic storage device, coupled to the bus 1202 for storing information and instructions to be executed by the processor 1204. The main memory 1206 also may be used for storing temporary variables or other intermediate information during execution of instructions to be executed by the processor 1204. The computer system 1200 further includes a read only memory (ROM) 1208 or other static storage device coupled to the bus 1202 for storing static information and instructions for the processor 1204. A data storage device 1210, such as a magnetic disk or optical disk, is provided and coupled to the bus 1202 for storing information and instructions.

The computer system 1200 may be coupled via the bus 1202 to a display 1212, such as a cathode ray tube (CRT), for displaying information to a user. An input device 1214, including alphanumeric and other keys, is coupled to the bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The computer system 1200 may be used for performing various functions (e.g., calculation) in accordance with the embodiments described herein. According to one embodiment, such use is provided by computer system 1200 in response to processor 1204 executing one or more sequences of one or more instructions contained in the main memory 1206. Such instructions may be read into the main memory 1206 from another computer-readable medium, such as storage device 1210. Execution of the sequences of instructions contained in the main memory 1206 causes the processor 1204 to perform the process steps described herein. One or more processors in a multi-processing arrangement may also be employed to execute the sequences of instructions contained in the main memory 1206. In alternative embodiments, hard-wired circuitry may be used in place of or in combination with software instructions to implement features of the embodiments described herein. Thus, embodiments described herein are not limited to any specific combination of hardware circuitry and software.

The term "computer-readable medium" as used herein refers to any medium that participates in providing instructions to the processor 1204 for execution. Such a medium may take many forms, including but not limited to, non-volatile media, volatile media, and transmission media. Non-volatile media includes, for example, optical or magnetic disks, such as the storage device 1210. A non-volatile medium may be considered to be an example of a non-transitory medium. Volatile media includes dynamic memory, such as the main memory 1206. A volatile medium may be considered to be another example of a non-transitory medium. Transmission media includes coaxial cables, copper wire and fiber optics, including the wires that comprise the bus 1202. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1204 for execution. For example, the instructions may initially be carried on a magnetic disk of a remote computer. The remote computer can load the instructions into its dynamic memory and send the instructions over a telephone line using a modem. A modem local to the computer system 1200 can receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1206, from which the processor 1204 retrieves and executes the instructions. The instructions received by the main memory 1206 may optionally be stored on the storage device 1210 either before or after execution by the processor 1204.

The computer system 1200 also includes a communication interface 1218 coupled to the bus 1202. The communication interface 1218 provides a two-way data communication coupling to a network link 1220 that is connected to a local network 1222. For example, the communication interface 1218 may be an integrated services digital network (ISDN) card or a modem to provide a data communication connection to a corresponding type of telephone line. As another example, the communication interface 1218 may be a local area network (LAN) card to provide a data communication connection to a compatible LAN. Wireless links may also be implemented. In any such implementation, the communication interface 1218 sends and receives electrical, electromagnetic or optical signals that carry data streams representing various types of information.

The network link 1220 typically provides data communication through one or more networks to other devices. For example, the network link 1220 may provide a connection through local network 1222 to a host computer 1224 or to equipment 1226 such as a radiation beam source or a switch operatively coupled to a radiation beam source. The data streams transported over the network link 1220 can comprise electrical, electromagnetic or optical signals. The signals through the various networks and the signals on the network link 1220 and through the communication interface 1218, which carry data to and from the computer system 1200, are exemplary forms of carrier waves transporting the information. The computer system 1200 can send messages and receive data, including program code, through the network (s), the network link 1220, and the communication interface 1218.

Although particular embodiments have been shown and described, it will be understood that it is not intended to limit the claimed inventions, and it will be obvious to those skilled in the art that various changes and modifications may be made. The specification and drawings are, accordingly, to be regarded in an illustrative rather than restrictive sense. The claimed inventions are intended to cover alternatives, modifications, and equivalents.

What is claimed:

1. A method of obtaining a volumetric image, comprising:
   obtaining a plurality of volumetric images, the volumetric images generated using respective sets of projection images, wherein the volumetric images and the respective sets of projection images correspond with different respective bins for a physiological cycle; and
   determining an additional volumetric image using one or more of the projection images from each of the sets that correspond with the different respective bins for the physiological cycle;
   wherein the act of determining the additional volumetric image is performed using a processor; and
   wherein the bins to which the sets of projection images correspond cover a phase or amplitude range that is at least 50% of a complete phase or amplitude range for the physiological cycle.

2. The method of claim 1, wherein the phase or amplitude range is at least 90% of the complete phase or amplitude range for the physiological cycle.

3. The method of claim 1, wherein the act of determining the additional volumetric image comprises:
   obtaining data regarding registrations of the volumetric images; and
   determining the additional volumetric image using the data and the one or more of the projection images from each of the sets.

4. The method of claim 3, wherein each of the registrations of the corresponding volumetric image comprises a registration between the corresponding volumetric image and a reference image.

5. The method of claim 1, wherein the act of determining the additional volumetric image is performed without modifying the one or more of the projection images.

6. A method of obtaining a volumetric image, comprising:
   obtaining a plurality of volumetric images, the volumetric images generated using respective sets of projection images, wherein the volumetric images and the respective sets of projection images correspond with different respective bins for a physiological cycle; and
   determining an additional volumetric image using one or more of the projection images from each of the sets that correspond with the different respective bins for the physiological cycle;
   wherein the act of determining the additional volumetric image is performed using a processor;
   wherein the act of determining the additional volumetric image comprises:
      obtaining data regarding registrations of the volumetric images; and
      determining the additional volumetric image using the data and the one or more of the projection images from each of the sets; and
   wherein each of the registrations of the corresponding volumetric image comprises a registration between the corresponding volumetric image and another one of the volumetric images that is adjacent to the corresponding volumetric image in bin order.

7. The method of claim 6, wherein the act of determining the additional volumetric image comprises:
   iteratively modifying one of the projection images from one of the sets using at least some of the data regarding two or more of the registrations; and
   using the modified projection image in an image reconstruction process to determine the additional volumetric image.

8. A method of obtaining a volumetric image, comprising:
   obtaining a plurality of volumetric images, the volumetric images generated using respective sets of projection images, wherein the volumetric images and the respective sets of projection images correspond with different respective bins for a physiological cycle; and
   determining an additional volumetric image using one or more of the projection images from each of the sets that correspond with the different respective bins for the physiological cycle;
   wherein the act of determining the additional volumetric image is performed using a processor;
   wherein the act of determining the additional volumetric image comprises:
      obtaining data regarding registrations of the volumetric images; and
      determining the additional volumetric image using the data and the one or more of the projection images from each of the sets; and
   wherein the data comprises a plurality of sets of vectors, each of the sets of vectors representing a deformation registration for respective one of the volumetric images.

9. The method of claim 8, wherein the additional volumetric image corresponds to a bin for the physiological cycle that is different from the bins to which the sets of projection images correspond.

10. The method of claim 8, wherein the act of determining the additional volumetric image is performed using at least 50% of all of the projection images from all of the sets.

11. The method of claim 8, wherein the act of determining the additional volumetric image is performed using at least 90% of all of the projection images from all of the sets.

12. The method of claim 8, wherein the sets comprise at least two sets.

13. A method of obtaining a volumetric image, comprising:
obtaining a plurality of volumetric images, the volumetric images generated using respective sets of projection images, wherein the volumetric images and the respective sets of projection images correspond with different respective bins for a physiological cycle; and
determining an additional volumetric image using one or more of the projection images from each of the sets that correspond with the different respective bins for the physiological cycle;
wherein the act of determining the additional volumetric image is performed using a processor; and
wherein the act of determining the additional volumetric image comprises:
modifying the one or more of the projection images from each of the sets; and
using the modified projection images to reconstruct the additional volumetric image.

14. The method of claim 13, wherein the additional volumetric image is for a phase or amplitude range of the physiological cycle, and the one or more of the projection images correspond with respective phases or amplitudes that are outside the phase or amplitude range.

15. A method of obtaining a volumetric image, comprising:
obtaining a plurality of volumetric images, the volumetric images generated using respective sets of projection images, wherein the volumetric images and the respective sets of projection images correspond with different respective bins for a physiological cycle; and
determining an additional volumetric image using one or more of the projection images from each of the sets that correspond with the different respective bins for the physiological cycle;
wherein the act of determining the additional volumetric image is performed using a processor; and
wherein the one or more of the projection images from each of the sets that are used to determine the additional volumetric image comprises two projection images from two respective ones of the sets; and
wherein the two projection images are separated by a phase or amplitude range that is at least 25% of a complete phase or amplitude range for the physiological cycle.

16. A computer product having a non-transitory computer-readable medium storing a set of instructions, an execution of which by a computer causes a process to be performed, the process comprising:
obtaining a plurality of volumetric images, the volumetric images generated using respective sets of projection images, wherein the volumetric images and the respective sets of projection images correspond with different respective bins for a physiological cycle; and
determining an additional volumetric image using one or more of the projection images from each of the sets that correspond with the different respective bins for the physiological cycle;
wherein the bins to which the sets of projection images correspond cover a phase or amplitude range that is at least 50% of a complete phase or amplitude range for the physiological cycle.

17. The computer product of claim 16, wherein the phase or amplitude range is at least 90% of the complete phase or amplitude range for the physiological cycle.

18. The computer product of claim 16, wherein the act of determining the additional volumetric image comprises:
obtaining data regarding registrations of the volumetric images; and
determining the additional volumetric image using the data and the one or more of the projection images from each of the sets.

19. The computer product of claim 18, wherein each of the registrations of the corresponding volumetric image comprises a registration between the corresponding volumetric image and a reference image.

20. The computer product of claim 16, wherein the act of determining the additional volumetric image is performed without modifying the one or more of the projection images.

21. A computer product having a non-transitory computer-readable medium storing a set of instructions, an execution of which by a computer causes a process to be performed, the process comprising:
obtaining a plurality of volumetric images, the volumetric images generated using respective sets of projection images, wherein the volumetric images and the respective sets of projection images correspond with different respective bins for a physiological cycle; and
determining an additional volumetric image using one or more of the projection images from each of the sets that correspond with the different respective bins for the physiological cycle;
wherein the act of determining the additional volumetric image comprises:
obtaining data regarding registrations of the volumetric images; and
determining the additional volumetric image using the data and the one or more of the projection images from each of the sets; and
wherein each of the registrations of the corresponding volumetric image comprises a registration between the corresponding volumetric image and another one of the volumetric images that is adjacent to the corresponding volumetric image in bin order.

22. The computer product of claim 21, wherein the act of determining the additional volumetric image comprises:
iteratively modifying one of the projection images from one of the sets using at least some of the data regarding two or more of the registrations; and
using the modified projection image in an image reconstruction process to determine the additional volumetric image.

23. A computer product having a non-transitory computer-readable medium storing a set of instructions, an execution of which by a computer causes a process to be performed, the process comprising:
obtaining a plurality of volumetric images, the volumetric images generated using respective sets of projection images, wherein the volumetric images and the respective sets of projection images correspond with different respective bins for a physiological cycle; and
determining an additional volumetric image using one or more of the projection images from each of the sets that correspond with the different respective bins for the physiological cycle;
wherein the act of determining the additional volumetric image comprises:
obtaining data regarding registrations of the volumetric images; and
determining the additional volumetric image using the data and the one or more of the projection images from each of the sets; and wherein the data comprises a plurality of sets of vectors, each of the sets of vectors representing a deformation registration for respective one of the volumetric images.

24. The computer product of claim 23, wherein the additional volumetric image corresponds to bin for the physiological cycle that is different from the bins to which the sets of projection images correspond.

25. The computer product of claim 23, wherein the act of determining the additional volumetric image is performed using at least 50% of all of the projection images from all of the sets.

26. The computer product of claim 23, wherein the act of determining the additional volumetric image is performed using at least 90% of all of the projection images from all of the sets.

27. The computer product of claim 23, wherein the sets comprise at least two sets.

28. A computer product having a non-transitory computer-readable medium storing a set of instructions, an execution of which by a computer causes a process to be performed, the process comprising:
    obtaining a plurality of volumetric images, the volumetric images generated using respective sets of projection images, wherein the volumetric images and the respective sets of projection images correspond with different respective bins for a physiological cycle; and
    determining an additional volumetric image using one or more of the projection images from each of the sets that correspond with the different respective bins for the physiological cycle;
    wherein the act of determining the additional volumetric image comprises:
        modifying the one or more of the projection images from each of the sets; and
        using the modified projection images to reconstruct the additional volumetric image.

29. The computer product of claim 28, wherein the additional volumetric image is for a phase or amplitude range of the physiological cycle, and the one or more of the projection images correspond with respective phases or amplitudes that are outside the phase range.

30. A computer product having a non-transitory computer-readable medium storing a set of instructions, an execution of which by a computer causes a process to be performed, the process comprising:
    obtaining a plurality of volumetric images, the volumetric images generated using respective sets of projection images, wherein the volumetric images and the respective sets of projection images correspond with different respective bins for a physiological cycle; and
    determining an additional volumetric image using one or more of the projection images from each of the sets that correspond with the different respective bins for the physiological cycle;
    wherein the one or more of the projection images from each of the sets that are used to determine the additional volumetric image comprises two projection images from two respective ones of the sets; and
    wherein the two projection images are separated by a phase or amplitude range that is at least 25% of a complete phase or amplitude range for the physiological cycle.

31. An apparatus for obtaining a volumetric image, comprising a processor, wherein the processor is configured for:
    obtaining a plurality of volumetric images, the volumetric images generated using respective sets of projection images, wherein the volumetric images and the respective sets of projection images correspond with different respective bins for a physiological cycle; and
    determining an additional volumetric image using one or more of the projection images from each of the sets that correspond with the different respective bins for the physiological cycle;
    wherein the bins to which the sets of projection images correspond cover a phase or amplitude range that is at least 50% of a complete phase or amplitude range for the physiological cycle.

32. The apparatus of claim 31, wherein the phase or amplitude range is at least 90% of the complete phase or amplitude range for the physiological cycle.

33. The apparatus of claim 31, wherein the processor is configured for determining the additional volumetric image by:
    obtaining data regarding registrations of the volumetric images; and
    determining the additional volumetric image using the data and the one or more of the projection images from each of the sets.

34. The apparatus of claim 33, wherein each of the registrations of the corresponding volumetric image comprises a registration between the corresponding volumetric image and a reference image.

35. The apparatus of claim 31, wherein the processor is configured to determine the additional volumetric image without modifying the one or more of the projection images.

36. An apparatus for obtaining a volumetric image, comprising a processor, wherein the processor is configured for:
    obtaining a plurality of volumetric images, the volumetric images generated using respective sets of projection images, wherein the volumetric images and the respective sets of projection images correspond with different respective bins for a physiological cycle; and
    determining an additional volumetric image using one or more of the projection images from each of the sets that correspond with the different respective bins for the physiological cycle;
    wherein the processor is configured for determining the additional volumetric image by:
        obtaining data regarding registrations of the volumetric images; and
        determining the additional volumetric image using the data and the one or more of the projection images from each of the sets; and
    wherein each of the registrations of the corresponding volumetric image comprises a registration between the corresponding volumetric image and another one of the volumetric images that is adjacent to the corresponding volumetric image in bin order.

37. The apparatus of claim 36, wherein the processor is configured for determining the additional volumetric image by:
    iteratively modifying one of the projection images from one of the sets using at least some of the data regarding two or more of the registrations; and
    using the modified projection image in an image reconstruction process to determine the additional volumetric image.

38. An apparatus for obtaining a volumetric image, comprising a processor, wherein the processor is configured for:
    obtaining a plurality of volumetric images, the volumetric images generated using respective sets of projection images, wherein the volumetric images and the respective sets of projection images correspond with different respective bins for a physiological cycle; and determining an additional volumetric image using one or more of the projection images from each of the sets that correspond with the different respective bins for the physiological cycle;

wherein the processor is configured for determining the additional volumetric image by:
    obtaining data regarding registrations of the volumetric images; and
    determining the additional volumetric image using the data and the one or more of the projection images from each of the sets; and wherein the data comprises a plurality of sets of vectors, each of the sets of vectors representing a deformation registration for respective one of the volumetric images.

39. The apparatus of claim 38, wherein the additional volumetric image corresponds to a bin for the physiological cycle that is different from the bins to which the sets of projection images correspond.

40. The apparatus of claim 38, wherein the processor is configured to use at least 50% of all of the projection images from all of the sets to determine the additional volumetric image.

41. The apparatus of claim 38, wherein the processor is configured to use at least 90% of all of the projection images from all of the sets to determine the additional volumetric image.

42. The apparatus of claim 38, wherein the sets comprise at least two sets.

43. An apparatus for obtaining a volumetric image, comprising a processor, wherein the processor is configured for:
    obtaining a plurality of volumetric images, the volumetric images generated using respective sets of projection images, wherein the volumetric images and the respective sets of projection images correspond with different respective bins for a physiological cycle; and
    determining an additional volumetric image using one or more of the projection images from each of the sets that correspond with the different respective bins for the physiological cycle;

wherein the processor is configured for determining the additional volumetric image by:
    modifying the one or more of the projection images from each of the sets; and
    using the modified projection images to reconstruct the additional volumetric image.

44. The apparatus of claim 43, wherein the additional volumetric image is for a phase or amplitude range of the physiological cycle, and the one or more of the projection images correspond with respective phases or amplitudes that are outside the phase range.

45. An apparatus for obtaining a volumetric image, comprising a processor, wherein the processor is configured for:
    obtaining a plurality of volumetric images, the volumetric images generated using respective sets of projection images, wherein the volumetric images and the respective sets of projection images correspond with different respective bins for a physiological cycle; and
    determining an additional volumetric image using one or more of the projection images from each of the sets that correspond with the different respective bins for the physiological cycle;

wherein the one or more of the projection images from each of the sets that are used to determine the additional volumetric image comprises two projection images from two respective ones of the sets; and wherein the two projection images are separated by a phase or amplitude range that is at least 25% of a complete phase or amplitude range for the physiological cycle.

\* \* \* \* \*